United States Patent [19]

Shank et al.

[11] Patent Number: 5,760,006
[45] Date of Patent: Jun. 2, 1998

[54] ANTICONVULSANT DERIVATIVES USEFUL IN TREATING PSORIASIS

[75] Inventors: Richard P. Shank, Blue Bell; Claudia K. Derian, Hatboro, both of Pa.

[73] Assignee: Ortho Pharmaceutical Corporation, Raritan, N.J.

[21] Appl. No.: 881,010

[22] Filed: Jun. 23, 1997

[51] Int. Cl.$^6$ .................................................. A61K 31/35
[52] U.S. Cl. .................. 514/23; 514/456; 514/459; 514/517; 514/863; 549/364; 549/426; 558/20; 558/48
[58] Field of Search ................. 549/364, 426; 514/456, 459, 517, 863, 23; 558/20, 48

[56] References Cited

U.S. PATENT DOCUMENTS 4,513,006  4/1985  Maryanoff et al. ................. 514/23
5,332,736  7/1994  Carmosin et al. ................. 514/235
5,498,629  3/1996  Costenzo et al. ................. 514/439

*Primary Examiner*—Thurman K. Page
*Assistant Examiner*—Lakshmi S. Channavajjala
*Attorney, Agent, or Firm*—Ralph R. Palo

[57] ABSTRACT

The use of compounds of the following formula I:

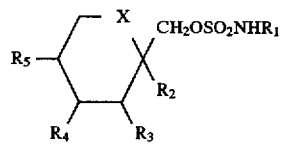

for treating psoriasis is disclosed.

4 Claims, No Drawings

ANTICONVULSANT DERIVATIVES USEFUL IN TREATING PSORIASIS

BACKGROUND OF THE INVENTION

Compounds of Formula I:

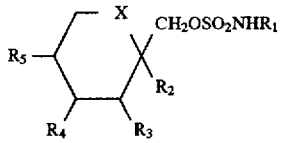

are structurally novel antiepileptic compounds that are highly effective anticonvulsants in animal tests (Maryanoff, B. E., Nortey, S. O., Gardocki, J. F., Shank, R. P. and Dodgson, S. P. *J. Med. Chem.* 30, 880–887, 1987; Maryanoff, B. E., Costanzo, M. J., Shank, R. P., Schupsky, J. J., Ortegon, M. E., and Vaught J. L. Bioorganic & Medicinal Chemistry Letters 3, 2653–2656, 1993, McComsey, D. F. and Maryanoff, B. E., J. Org. Chem. 1995). These compounds are covered by U.S. Pat. No. 4,513,006. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., Epilepsia 36 (S4) 33,1995; S. K. SACHDEO, R. C. SACHDEO, R. A. REIFE, P. LIM and G. PLEDGER, Epilepsia 36(S4) 33, 1995), and is currently marketed for the treatment of simple and complex partial seizure epilepsy with or without secondary generalized seizures in Great Britain, Finland, the United States and Sweden and applications for regulatory approval are presently pending in numerous countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., Epilepsia 25 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. Pharmacol. 254 83–89,1994), and in an animal model of kindled epilepsy (A. WAUQUIER and S. ZHOU, Epilepsy Res. 24, 73–77, 1996).

Recent preclinical studies on topiramate have revealed previously unrecognized pharmacological properties which suggest that topiramate should be effective in treating some other disorders. One of these is psoriasis.

DISCLOSURE OF THE INVENTION

Accordingly, it has been found that compounds of the following formula I:

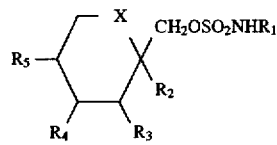

wherein X is O or $CH_2$, and $R_1$, $R_2$, $R_3$, $R_4$ and $R_5$ are as defined hereinafter are useful in treating psoriasis.

DETAILED DESCRIPTION OF THE PREFERRED EMBODIMENTS

The sulfamates of the invention are of the following formula (I):

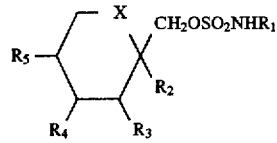

wherein

X is $CH_2$ or oxygen;

$R_1$ is hydrogen or alkyl; and $R_2$, $R_3$, $R_4$ and $R_5$ are independently hydrogen or lower alkoxy, when X is oxygen, $R_2$ and $R_3$ and/or $R_4$ and $R_5$ together may be a methylenedioxy group of the following formula (II):

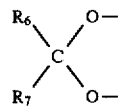

wherein $R_6$ and $R_7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl.

A particular group of compounds of formula (I) are those wherein X is oxygen and both $R_2$ and $R_3$, and $R_4$ and $R_5$ together are methylenedioxy groups of the formula (II), wherein $R_6$ and $R_7$ are both hydrogen, both alkyl, or combine to form a spiro cyclopentyl or cyclohexyl ring, in particular where $R_6$ and $R_7$ are both alkyl such as methyl. A second group of compounds are those wherein X is $CH_2$ and $R_4$ and $R_5$ are joined to form a benzene ring. A third group of compounds of formula (I) are those wherein both $R_2$ and $R_3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium a-butoxide or sodium hydride at a temperature of about −20° to 25° C. and in a solvent such as toluene, THF or dimethylformamide wherein R is a moiety of the following formula (III):

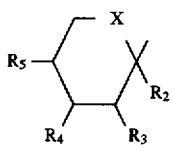

(b) Reaction of an alcohol of the formula $RCH_2OH$ with sulfurylchloride of the formula $SO_2Cl_2$ in the presence of a base such as triethylamine or pyridine at a temperature of about $-40°$ to $25°$ C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of abut $40°$ to $25°$ C. in a solvent such as methylene chloride or acetonitrile to produce a compound of formula (I). The reaction conditions for (b) are also described by T. Tsuchiya et al. in Tet. Letters, No. 36, p.3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in Tet. Lett. p. 2455-2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$, and $R_4$ and $R_5$ are identical and are of the formula (II) may be obtained by the method of R. F. Brady in Carbohydrate Research, Vol. 14, p. 35 to 40 (1970) or by reaction of the trimethylsilyl enol ether of a $R_6COR_7$ ketone or aldehyde with fructose at a temperature of about $25°$ C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in J. Org. Chem. Vol. 38, No. 22, p. 3935 (1973).

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such a diglyme, THF or toluene at a temperature of about $0°$ to $100°$ C., e.g. as described by H. O. House in "Modern Synthetic Reactions", 2nd Ed., pages 45 to 144 (1972).

The compounds of formula I: may also be made by the process disclosed U.S. Pat. No. 4,513,006, which is incorporated by reference herein.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygens of the methylenedioxy group (II) are attached on the same side of the 6-membered ring.

The activity of the compounds of formula I in treating psoriasis was first evidenced in clinical studies conducted to evaluate the efficacy of topiramate in treating epilepsy. At least three patients who coincidentally had psoriasis reported that there was a marked reduction in the psoriatic lesions. Therefore, preclinical in vitro studies were conducted to evaluate the effects of topiramate on keratinocyte function as a putative mechanism of action for its potential beneficial effects in treating psoriasis. One of the hallmarks of psoriatic lesions is hyperproliferative epidermal keratinocytes. In general, agents that affect the proliferation of keratinocytes have an inverse effect on differentiation, i.e. they would inhibit growth and enhance differentiation. Two measures of keratinocyte function were therefore evaluated: cell growth and differentiation.

In these studies, keratinocytes were grown in Medium154, a low calcium medium supplemented with bovine pituitary extract (BPE), bovine insulin, bovine transferrin, human epidermal growth factor (EGF) and hydrocortisone. Keratinocytes were grown to 60-80% confluence and subcultured by using trypsin/EDTA.

Four separate experiments were performed to evaluate the dose-dependent effect of topiramate on keratinocyte cell growth as measured by maturity after six days of treatment. Topiramate was dissolved in DMSO to make a 100 mM stock solution. In all experiments the final concentration of DMSO in the cell incubation medium was 0.1%. Vehicle controls (0.1% DMSO) were included in each experiment. Cell growth was induced by a combination of the growth factors EGF and BPE. Topiramate had a modest inhibitory effect on cell growth under these assay conditions; however, no dose dependence was observed (R.W Johnson Pharmaceutical Research Institute Laboratory Notebook No. 12183 and 12540). The maximal response was observed at 10 micromolar, 32±10% inhibition. While there was a trend toward inhibition of cell growth, this did not reach statistical significance ($p > 0.05$).

The effect of topiramate on keratinocyte differentiation was measured by the expression of transglutaminase-1 protein after three days of treatment. Three separate experiments were performed. Differentiation was evaluated in both low calcium and high calcium incubation conditions. An increase in differentiation would be most readily observed under low calcium conditions whereas an inhibition of differentiation could be detected under conditions of high calcium-induced differentiation. Topiramate caused a modest increase in transglutaminase-1 protein with both conditions, indicating an enhancing effect. A follow-up study was conducted which extended the incubation time to 5 days to look for further enhancement. No additional increases in transglutaminase-1 were observed in this latter study.

The results of these studies indicate that topiramate's effects on keratinocyte function are consistent with those expected for an agent that would affect the hyperproliferative keratinocyte response associated with psoriasis; inhibition of cell growth and enhancement of differentiation.

For treating psoriasis, a compound of formula (I) may be employed at a daily dosage in the range of about 50 to 400 mg administered orally, usually in two divided doses, for an average adult human. A unit dose would contain about 25 to 200 mg of the active ingredient. Alternatively, a compound of formula (I) may be administered topically to the affected area of the skin once or twice daily at a dosage in the range of 5 to 50 mg.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa-butter could be used as the carrier. For parenterals, the carrier will usually comprise sterile water, though other ingredients, for example, for purposes such as aiding solubility or for preservation, may be included. Injectable suspensions may also be prepared in which case appropriate liquid carriers, suspending agents and the like may be employed.

Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder injection, teaspoonful, suppository and the like from about 25 to about 200 mg of the active ingredient.

What is claimed is:

1. A method for treating psoriasis comprising administering to a human afflicted with such condition a therapeutically effective amount for treating such condition of a compound of the formula I:

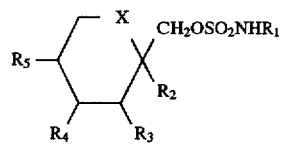

wherein

X is $CH_2$ or oxygen;

$R_1$ is hydrogen or alkyl; and $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

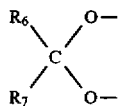

wherein $R_6$ and $R_7$ are the same or different and are hydrogen, lower alkyl or are alkyl and are joined to form a cyclopentyl or cyclohexyl ring.

2. The method of claim 1 wherein the compound of formula I is topiramate.

3. The method of claim 1, wherein the therapeutically effective amount is of from about 50 to 400 mg.

4. The method of claim 1, wherein the amount is of from about 25 to 200 mg.

* * * * *

UNITED STATES PATENT AND TRADEMARK OFFICE
CERTIFICATE OF CORRECTION

PATENT NO. : 5,760,006
DATED : Jun. 2, 1998
INVENTOR(S) : Richard P. Shak, Claudia K. Derian It is certified that error appears in the above-indentified patent and that said Letters Patent is hereby corrected as shown below:

Column 1, Line 48 delete "25" and insert -- 35 --.

Signed and Sealed this

Sixteenth Day of March, 1999

Attest:

Q. TODD DICKINSON

*Attesting Officer*   *Acting Commissioner of Patents and Trademarks*